United States Patent [19]

Kowalski

[11] Patent Number: 4,520,800
[45] Date of Patent: Jun. 4, 1985

[54] PATIENT TREATMENT TABLE

[75] Inventor: Frank P. Kowalski, Des Plaines, Ill.

[73] Assignee: Standex International Corporation, Salem, N.H.

[21] Appl. No.: 493,145

[22] Filed: May 9, 1983

[51] Int. Cl.³ .............................................. A61F 5/00
[52] U.S. Cl. ..................................................... 128/72
[58] Field of Search ................................... 128/68–75, 128/33; 5/63–69, 70, 79; 269/322–326

[56] References Cited

U.S. PATENT DOCUMENTS

| | | |
|---|---|---|
| 1,018,757 | 2/1912 | Grady .............................. 128/70 X |
| 2,152,734 | 4/1939 | Ford . |
| 2,193,882 | 3/1940 | Petersen ................................. 128/70 |
| 2,492,406 | 12/1949 | Thomas .................................. 128/33 |
| 2,656,469 | 10/1953 | Laur . |
| 2,693,796 | 11/1954 | Warner ........................... 128/70 X |
| 2,738,975 | 3/1956 | Zaboy . |
| 2,756,809 | 7/1956 | Endresen . |
| 2,764,150 | 9/1956 | Ettinger et al. . |
| 3,640,520 | 2/1972 | Wieland et al. . |
| 3,806,968 | 4/1974 | Robey . |
| 3,821,952 | 7/1974 | Binegar ................................. 128/70 |
| 4,131,802 | 12/1978 | Braden et al. . |
| 4,153,293 | 5/1979 | Sheldon . |
| 4,166,459 | 9/1979 | Nightengale .......................... 128/75 |
| 4,207,635 | 6/1980 | Leroy . |
| 4,309,058 | 1/1982 | Barley . |

OTHER PUBLICATIONS

2 Page brochure entitled "Product Data–Fischer X–Ray–The Chemonucleolysis Table".
3 Photos of Chemonucleolysis Table, (unidentified origin), bearing notation "Lumbar Elevator-Prototype".

Primary Examiner—Robert A. Hafer
Assistant Examiner—Chris Coppens
Attorney, Agent, or Firm—Mason, Kolehmainen, Rathburn & Wyss

[57] ABSTRACT

A patient treatment table includes a table frame, a hip board fixedly secured to said frame and a head board fixedly secured to said frame and spaced from said hip board. A transparent flexible arch member, of such thickness that it can maintain an adjustable height position under the patient's weight without requiring edge reinforcement, is pivotally mounted to said frame adjacent to and below the top surface of said head board and a slide member extending across the table beneath the edge of said hip board provides a pivotal support for the other end of said arch member. Said slide member may be adjusted relative to said hip board by means of an enclosed, motor driven lead screw actuator to bow said arch member upwardly from a minimum height position in which the top surface of the arch member is substantially the same as the upper surfaces of said head and hip boards. Suitable indicia are provided on the slide and table frame, calibrated in terms of the actual height of the top surface of the transparent arch, so that continuity of treatment and repeatablity of adjustment of the height of the arch can be achieved. The actuator is controllable by switch means located adjacent said arch member on either side of the table.

12 Claims, 16 Drawing Figures

PATIENT TREATMENT TABLE

The present invention relates to medical treatment tables, and more particularly, to a medical treatment table which is particularly adapted to facilitate treatments which may involve the use of X-ray equipment, such as the treatment of a patient who is suffering from a herniated disc.

A back treatment technique which has been named chemonucleolysis, requires insertion of a long needle into the back of the patient and into the herniated disk between two vertabrae. After the needle has been properly located, a solution of chymopapain is injected into the disc and dissolves the herniated material without affecting the outer portion of the disc. In order to assist the doctor during insertion of the needle and in order to locate the needle properly, an X ray image intensifier system is usually employed which includes a mobile unit having a C-shaped arm which includes portions which must be positioned above and below the patient's back so that an X-ray picture is displayed on the screen of the system while the needle is being inserted. During this procedure frequent changes in the position and angle of the C-arm unit are required.

During a chemonucleolysis treatment the patient is placed on his side on a table provided with an upwardly bowed or arched transparent section in the area of the patient's back which functions to separate the vertebrae in a particular area and facilitate insertion of the needle into the herniated disc at the desired location while the doctor watches the image intensifier screen. The C-arm image intensifier unit may require adjustment in order to obtain a clearly focused picture on the screen and it may also be desirable for the doctor to make prompt and precise adjustments in the height of the table, either for his ease and comfort in the difficult mechanical operation of inserting the needle, or to shift the position of the patient's vertebrae relative to the image intensifier units carried by the mobile C-arm and positioned above and below the patient's back. It is also sometimes necessary to make prompt and precise adjustments of the height of the transparent arch section of the table so as to open or close the vertebral space by bending the patient's back, in order to insert the needle at exactly the desired location.

Certain chemonucleolysis treatment tables have been heretofore proposed in which the height of a transparent upwardly bowed arch section can be adjusted manually. However, neither of the two chemonucleolysis tables of which applicant is aware is particularly suited for use with X-ray equipment, such as a mobile C arm image intensifier unit, because structural portions of the table in the space between the arch and the floor prevent convenient and prompt positioning and adjustment of the C arm unit. Furthermore, their essential elements cannot be adjusted quickly and precisely. In one such arrangement an adjustable arch assembly is laid across an opening in the top of the table and may be adjusted in height by means of a removable crank. In another arrangement, the height of the arch is adjusted by means of a crank permanently located at the foot of the table, adjustment of this crank acting to move the entire hip board portion of the table when the bow of the arch is to be changed. Such an arrangement tends to move the patient relative to the X-ray unit so that an X-ray picture of a different portion of the patient's back is produced and may necessitate repositioning of the X-ray image intensifier unit. Furthermore, such an adjustment cannot be done smoothly and quickly which is essential in medical procedures. Also, an arrangement which produces movement of the hip board relative to the skin of a patient lying on the table may cause discomfort and annoyance. In such other arrangment the height of each end of the table can be adjusted manually by means of individual cranks located beneath the table at each end thereof. However, such adjustment either requires additional personnel at each end of the table or requires the doctor to make individual adjustments himself which of course interferes with the needle insertion operation. Also, such table height adjustment cannot be done smoothly and quickly.

In both such prior art arrangements the arch section is made of relatively thin clear plastic such as plexiglass or other acrylic material, and requires reinforcing side walls at the edges of the arch to provide the strength necessary to support a patient. These sidewalls are subjected to repeated flexing as the bow of the arch is adjusted during use which can materially shorten the life of the arch. Also, in both of these prior art arrangements it is not possible to lower the arch so that its high point is even with the top of the table. This necessitates lifting the patient over the arch when he is placed on or removed from the table, with consequent difficulties and strain to both the attendants and the patient. Furthermore, neither of these prior art arrangements provide any means for indicating the actual height to which the arch has been adjusted, it being necessary for the doctor to guess whether the arch has been adjusted to the same height as a previous patient, or a patient having similar physical characteristics. As a result, continuity of treatment and repeatability of height adjustment from one patient to the next is not possible with these prior art arrangements.

It is, therefore, an object of the present invention to provide a new and improved patient treatment table which avoids one or more of the above discussed disadvantages of the prior art arrangements.

It is another object of the present invention to provide a new and improved patient treatment table in which the height of a transparent arch portion and the height of the table may be automatically, conveniently and precisely adjusted by means of finger tip controls readily accessible to the doctor as he treats a patient or views an X-ray image intensifier screen.

It is a further object of the present invention to provide a new and improved patient treatment table which enables a doctor to position, adjust, or put pressure on a patient's body to enhance any one of a variety of procedures such as orthopedic or urological procedures.

It is still another object of the present invention to provide a new and improved patient treatment table in which said finger tip controls are provided on both sides of the table, thereby to permit the doctor or his assistants to make automatic adjustments from either side of the table.

It is a still further object of the present invention to provide a new and improved patient treatment table in which the height of an adjustable transparent arch portion of the table is accurately indicated so that continuity of treatment and repeatability of adjustment from one patient to the next can be achieved.

It is a further object of the present invention to provide a new and improved chemonucleolysis treatment table in which the height of a transparent arch is precisely controllable and adjustable by means of a motor driven lead screw actuator which is controllable by the doctor during the needle insertion operation.

It is another object of the present invention to provide a new and improved chemonucleolysis treatment table in which the height of the table is precisely controllable and adjustable by means of separate motor driven lead screw actuators contained within each end of the table which are controllable by the doctor during the needle insertion operation.

It is still another object of the present invention to provide a new and improved patient treatment table in which the head end of the table may be lowered and the foot end of the table simultaneously raised by power driven means conveniently controllable by the doctor.

It is a further object of the invention to provide a new and improved patient treatment table in which a transparent adjustable arch portion of the table may be moved to a minimum height position in which the top surface of the arch is at the same height as the upper surface of the adjoining table portions and can support a substantial weight when in said minimum height position.

It is another object of the present invention to provide a new and improved chemonucleolysis treatment table in which one end of a transparent bowed arch portion is pivotally and fixedly mounted on the frame of the table and the other end thereof is movable toward said one end portion without producing movement of the table top portion adjacent thereto.

It is a further object of the present invention to provide a new and improved patient treatment table in which an adjustable arch consisting solely of a transparent sheet of vinyl material having substantial thickness is pivotally supported along the length of opposed edges thereof to provide a simplified long life construction which will support the weight of a heavy patient and can withstand repeated flexing without crazing, cracking, breaking, or unduly stressing the edges thereof.

Briefly considered, the patient treatment table of the present invention includes a table frame, a hip board fixedly secured to said frame and a head board fixedly secured to said frame and spaced from said hip board. A transparent flexible arch member, of such thickness that it can maintain an adjustable height position under the patient's weight without requiring edge reinforcement, is pivotally mounted to said frame adjacent to and below the top surface of said head board and a slide member extending across the table beneath the edge of said hip board provides a pivotal support for the other end of said arch member. Said slide member may be adjusted relative to said hip board by means of an enclosed, motor driven lead screw actuator to bow said arch member upwardly from a minimum height position in which the top surface of the arch member is substantially the same as the upper surfaces of said head and hip boards. Suitable indicia are provided on the slide and table frame, calibrated in terms of the actual height of the top surface of the transparent arch, so that continuity of treatment and repeatability of adjustment of the height of the arch can be achieved. The actuator is controllable by switch means located adjacent said arch member on either side of the table so that the doctor can make minute and precisely controllable adjustments of the height of said arch member during a treatment or operation which may involve continuous X-ray monitoring of a patient lying on the table.

The height of the table is also quickly and precisely made by means of separate motor driven lead screw actuators so that in performing chemonucleolysis treatments, which involve the mechanical operation of insertion of a long needle into the patient's back, the height of the table can be readily adjusted for different doctors and to accommodate different sized patients, thereby facilitating the precise positioning of the needle by the doctor. The actuators, which are enclosed at each end of the table, are controllable by switch means accessible to the doctor on either side of the table near the arch so that the space beneath the arch is entirely free to permit easy positioning and adjustment of a mobile C arm image intensifier unit relative to a patient on the table. These actuators are normally controlled to move the opposite ends of the table in the same direction so that the table is raised or lowered while remaining horizontal. However, by means of a selector switch also readily accessible to and convenient for the doctor these actuators may be controlled to move in opposite directions so that the foot end of the table is raised and the head end of the table is simultaneously lowered so that the table is rapidly moved to approximate the so-called Trendelenburg position in which the patient's feet are elevated with respect to his head.

The invention both as to its organization and method of operation, together with further objects and advantages thereof, will best be understood by reference to the following specification taken in connection with the accompanying drawings, in which:

FIG. 8 is a cross sectional view taken along the lines 8—8 of FIG. 7;

Figures 4, 5:
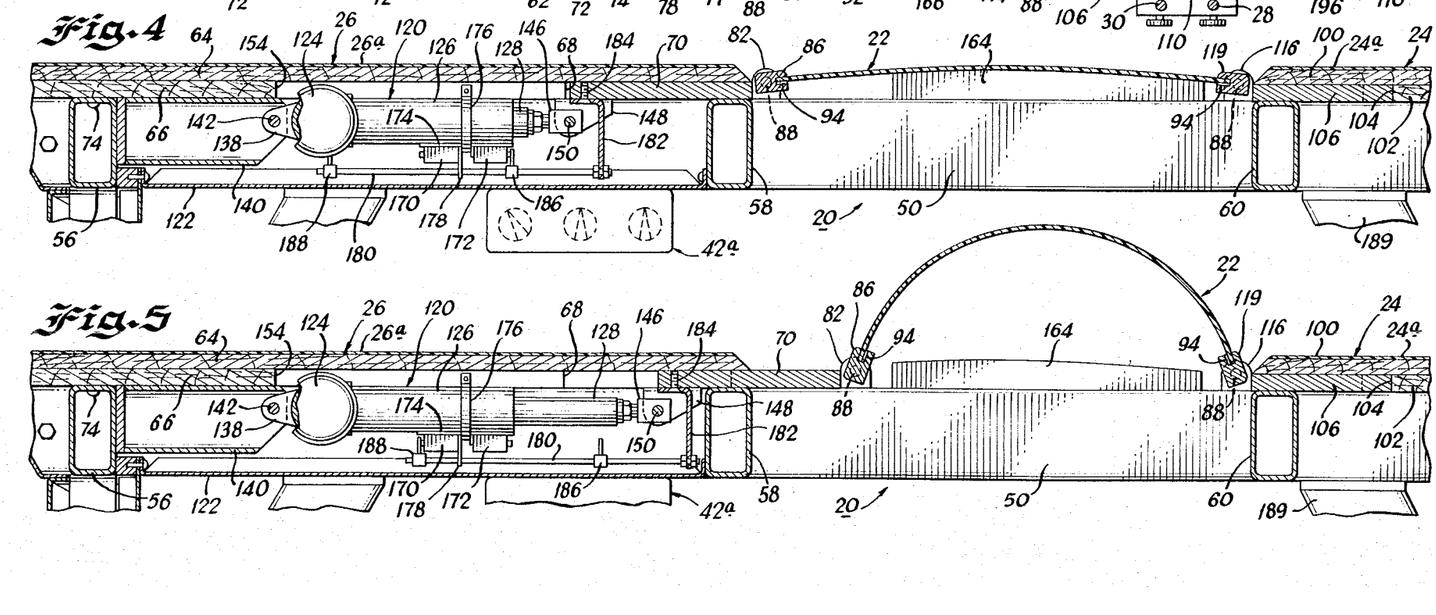
FIG. 4 is a cross sectional view taken along the line 4—4 of FIG. 3 and showing the arch member in a minimum height position.
FIG. 5 is a view similar to FIG. 4 but showing the arch member in a maximum height position.

Referring now to the drawings, the patient treatment table of the present invention is indicated generally at 20, this table being provided with a transparent flexible arch member 22 which is pivotally mounted between a head board portion 24 and a hip board portion 26. When the arch member 22 is in the minimum height position shown in FIGS. 1 and 4, a patient may be laid upon the table 20 and placed on his side with a minimum amount of effort, the arms of the patient being supported in the adjustable arm rests 28, 30. The arch member 22 may then be bowed upwardly by movement of the pivotally mounted end thereof relative to the hip board 26 to a desired elevated position, as shown in FIG. 5. While the table 20 is particularly suited for and will be described in connection with a chemonucleolysis treatment, it should be understood that the table 20 of the present invention is also particularly suitable for use in connection with other type of treatments or operations some of which may involve the use of X-ray equipment, such as a mobile C-arm image intensifier unit.

Figure 1:
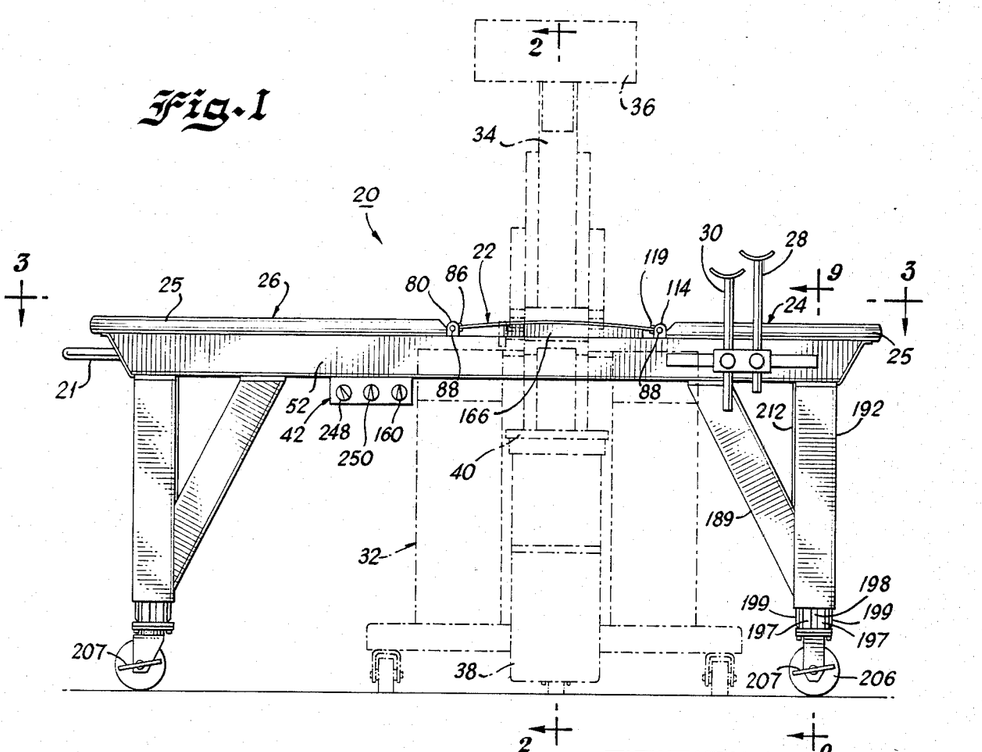
FIG. 1 is a front elevation view of the chemonucleolysis treatment table of the present invention shown in association with a C-arm image intensifier unit.
Figure 2:
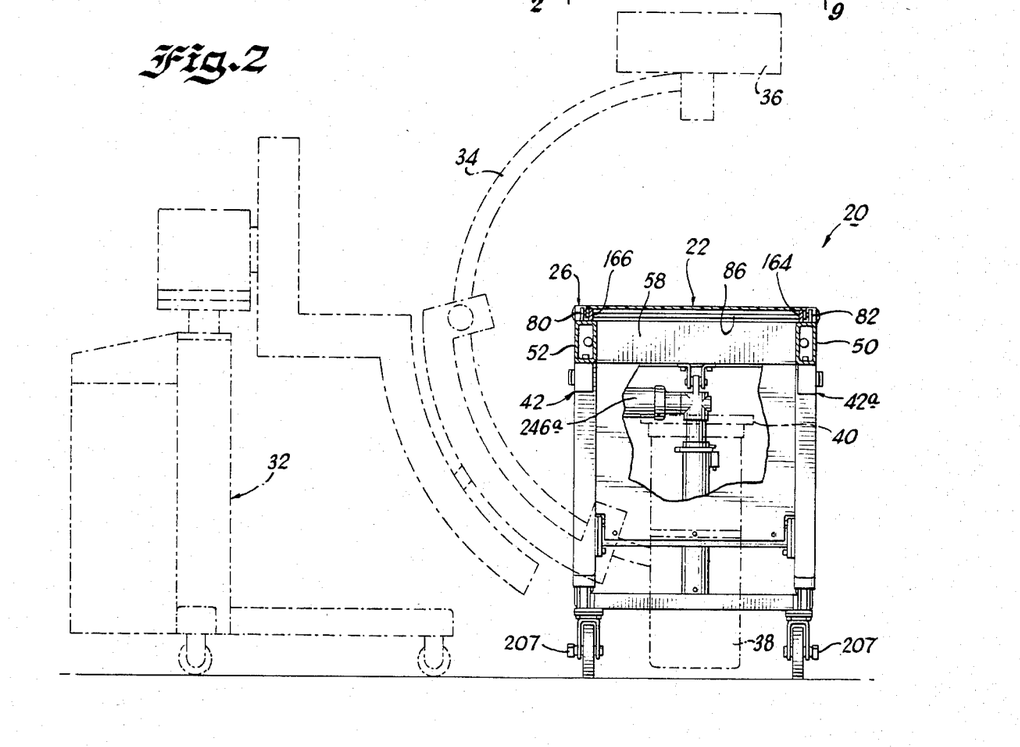
FIG. 2 is a sectional view taken along the lines 2—2 of FIG. 1.

As best illustrated in FIGS. 1 and 2, the chemonucleolysis treatment table 20 of the present invention is arranged to cooperate with a mobile X-ray image intensifier unit indicated generally at 32 of the so called C-arm type of construction in which a C-shaped support arm 34, which is adjustable relative to the frame of the mobile unit 32 carries an X-ray source indicated generally at 36 which is positioned above the back of a patient on the table 20 and a cylindrical image tube 38 which is positioned beneath the transparent section 22 of the table 20 and may include a cassette holder 40 for X-ray film.

In accordance with an important aspect of the present invention control panels 42 and 42a are provided on either side of the table 20 adjacent the transparent arch section 22 therof. By means of control switches located on the panels 42, 42a the doctor may selectively raise or lower the height of the table 20, by controlling motor driven actuators to be described in more detail hereinafter, so that the patient may be quickly and smoothly positioned at the most convenient height, taking into account the dimensions of the patient and the height of the doctor, to facilitate the difficult mechanical operation of insertion of a long needle into the patient's back. The doctor is also able to make precise and minute adjustments of the height of the table if such are necessary to obtain the clearest possible picture on the image intensifier screen as the needle is being inserted into the patient's back. In a similar manner, the control panels 42, 42a include suitable switch means which the doctor may actuate to vary the height of the transparent arch section 22 by controlling a separate motor driven actuator, as will be described in more detail hereinafter. As a result, the doctor can accurately control the height of the arch section 22 so as to open or close the vertebral space, by bending the patient's back, to facilitate the needle insertion operation. In addition, adjustment of the height of the arch 22 can be used in other types of treatments, such as putting pressure on the abdomen, when the patient is lying face down in connection with urological procedures.

Considering now the manner in which the flexible arch portion 22 is pivotally mounted and moved in accordance with the present invention, the table 20 includes a horizontal frame consisting of the tubular side bars 50, 52 which extend along the length of the table, and a series of tubular cross bars 56, 58, 60 and 62 which are welded to the side bars 50, 52 to provide a rigid horizontal frame for the table. The hip board 26 comprises an upper member 64 and a lower member 66, both preferably of wood, the lower member 66 being cut away to provide a recess 68 (FIG. 6) within which is positioned a movable arch slide bracket 70. Preferably, both the hip board 26 and head board 24 are covered with a sheet of formica 26a and 24a, respectively, and the edges of the head and hip boards are protected by an edge strip 25.

The hip board 24 is secured to the frame members 50, 52 and the cross member 56 by first inserting a series of T nuts 72 into the upper surface of the bottom member 66 before the members 64 and 66 are secured together as by gluing, the bottom member 66 being secured to the frame members 50, 52 by means of the bolts 74 which extend upwardly from the inside of the tubular members 50, 52 into the T nuts 72, the bolts 74 being accessible through access holes 76 in the bottom edge of the frame members 50, 52 and 56. The movable arch slide bracket 70 includes a pair of pivot supports 80, 82 which are secured to the ends of the bracket 70 by means of the screws 84. The bracket 70 is slideably mounted within the recess 68 on the frame members 50, 52 by providing the elongated slots 78 in the ends of the bracket 70 and mounting a pair of shouldered guide keys 77 within the slots 78 by means of the bolts 79 which extend into the side bars 50, 52, the slots 78 being provided with shoulder portions 78a (FIG. 6) which receive the upper shoulder portion 77a of the guide keys 77 so as to prevent the bracket 70 from moving upwardly as it slides along the frame members 50, 52.

In order to mount the transparent flexible arch members 22 so that the end portions thereof are securely clamped but are free to pivot as the arch is bowed upwardly, so that areas of high stress concentration are not set up in these end portions, an arch pivot bracket 86, which extends across the width of the table, is pivotally mounted in the end members 80, 82 by means of the pins 88, plastic, flanged bearings 90 being provided between the pins 88 and the end pivots 82 to ensure maximum freedom of rotation of the bracket 86. The arch pivot bracket 86 is provided with a slot 92 which receives the end portion 22a (FIG. 8) of the transparent arch member 22 together with a thin sheet metal clamping strip 94. The end 22a is clamped within the slot 92 by means of the screws 96 which engage the clamping strip 94 and produce a dimple therein which facilitates retaining of the end portion 22a of the arch 22 within the slot 92 without damaging the end portion 22a as would be the case if the screws 96 were directly inserted in the end portion 22a.

In an entirely similar manner the head board 24 comprises the upper member 100 and lower member 102, the lower member 102 being undercut to provide the recess 104 (FIG. 3) within which is positioned a fixed mounting bracket 106, the bracket 106 being secured to the frame members 50 and 52 by means of the screws 108. The upper and lower members 100 and 102 of the head board 24 are secured together by means of the bolts 110 which are accessible through the access holes 112 in the bottom edge of the frame members 50, 52 and 62. The end pivot supports 114 and 116 are secured to the ends of the bracket 106 by means of the screws 118 and pivotally support an arch pivot bracket 119 which extends along the width of the table and is pivotally mounted in the brackets 114, 116 in a manner identical to that described above in connection with the bracket 86. The end of the transparent arch section 22 is supported within a slot in the bracket 119 in a manner identical to that described heretofore in connection with the bracket 86. With the arrangement of the present invention a substantial load may be placed on the arch 22 and yet both ends of the transparent arch member 22 are entirely free to assume a curve corresponding to the bowed portion of the member 22 as this member is flexed upwardly to the maximum height position shown in FIG. 5. As a result, no local areas of high stress concentration are produced in the member 22 so that this member may be moved between its minimum and maximum height positions over long periods of time without wearing out.

Figure 3:
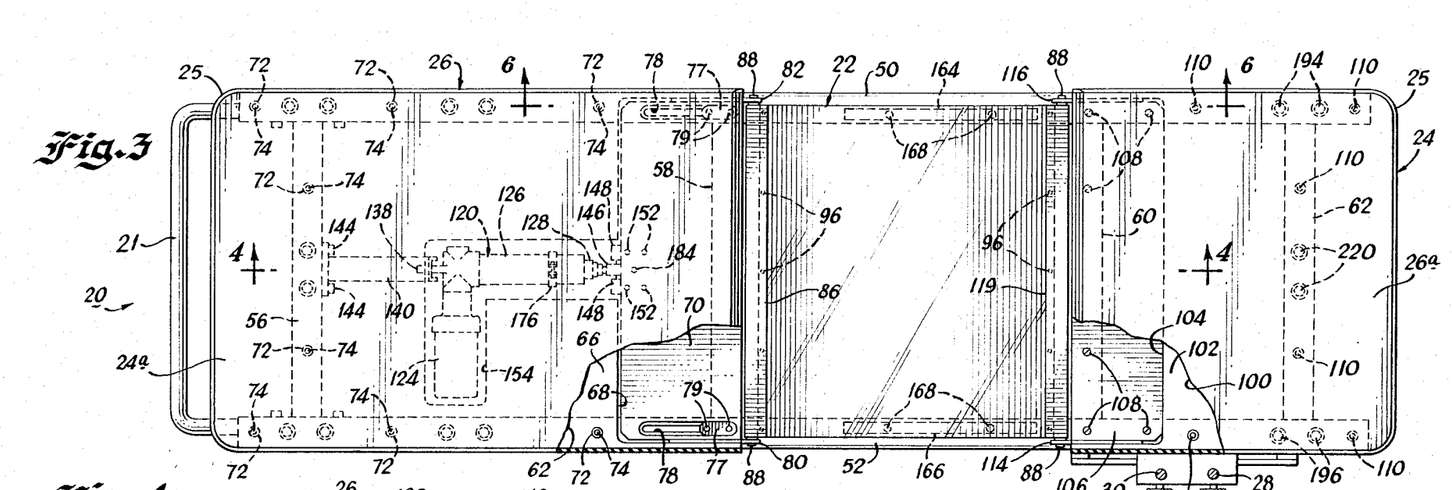
FIG. 3 is a top elevation view of the table of FIG. 1.

Considering now the manner in which the arch 22 may be quickly and precisely adjusted between the minimum and maximum height positions in accordance with the present invention, a motor driven lead screw actuator indicated generally at 120 is mounted beneath the hip board 26 and is totally enclosed by means of the bottom cover plate 122 which extends between the cross pieces 56 and 58 and is secured thereto. More particularly, the actuator 120 comprises an electric motor 124 which is interconnected with a lead screw actuator 126 through a suitable gearing arrangement so that the translating output member 128 of the actuator 120 may be smoothly and precisely moved to a desired position by energizing the motor 124 for a predetermined length of time. The pivot mount 138 of the actuator 120 is pivotally connected to a horizontal bracket 140 by means of the pin 142, the bracket 140 being secured to the cross bar 56 by means of the screws 144 (FIG. 3). The clevis 146 provided on the end of the translating tube 128 is pivotally connected to brackets 148 by means of the pins 150, the bracket 148 being secured to the underside of the slide bracket 70 by means of the screws 152 (FIG. 3). The lower member 66 of the hip board 26 is provided with an additional cut away portion 154 which provides suitable clearance for mounting the actuator 120 and communicates with the recess 68 provided for the slide 70.

Figure 12:
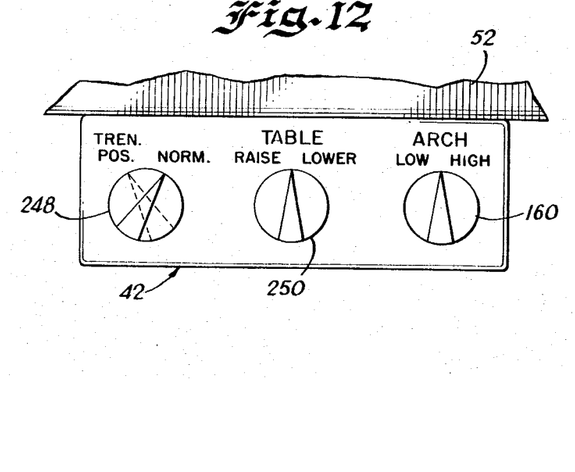
FIG. 12 is an enlarged elevational view of the control box portion of FIG. 1.

As best illustrated in FIG. 12, the control boxes 42 and 42a are each provided with a control knob 160 which is spring biased to the neutral position shown in FIG. 12. In this connection it is pointed out that the control boxes 42, 42a may be eliminated, if desired, and the controls thereof mounted inside the side bars 50, 52 with the control knobs mounted on the sides of the side bars. Such an arrangement has the advantage that the space below the side bars 50, 52 is completely free to allow for movement and adjustment of the mobile C-arm unit 32.

When the knob 160 is moved to the right and held in that position, the motor 124 is energized so as to extend the translating tube 128 and move the slide 70 to the right, as viewed in FIG. 4 so that the transparent arch member 22 may be bowed upwardly. Movement of the slide 70 continues until the doctor releases the knob 160 which is then spring biased back to neutral position shown in FIG. 12 and deenergizes the motor 124. In a similar manner rotation of the knob 160 in a counterclockwise direction to the lefthand position energizes the motor 124 to move the slide 70 in the opposite direction so as to lower the transparent arch section 22 of the table 20. While the motor driven lead screw actuator 120 is particularly suitable as a driving means for the slide 70, because of its compactness, power output and ease of installation and servicing, it will be understood that any other readily controllable drive means, such as a pneumatic or hydraulic actuator may be used. However, such actuators require a pressurized fluid medium, rather than electricity which is readily available in hospitals.

In accordance with an important aspect of the invention, the transparent arch 22 is made of a material which will transmit X-rays without substantial absorption or other deleterious effects, which will not fog or discolor when subjected to ultraviolet light, and is of substantial thickness so that it can support the weight of a heavy patient without requiring the side flanges of prior art arrangements which would tend to crack and break under repeated flexing of the arch member. Preferably, the transparent arch section 22 has a thickness of approximately 3/16 of an inch and is made of a vinyl compound such as cellulosic butylrate manufactured by Eastman Kodak under the tradename Uvex, which is ultraviolet light stabilized and has a high resistance to fatique so that it can withstand repeated flexing to the maximum height position shown in FIG. 5 without crazing, cracking or breaking. Also, as pointed out heretofore, the strain free mounting of the end portions of the arch 22 contributes greatly to the long life characteristics of the member 22 under repeated flexing during use.

Figures 6, 7:
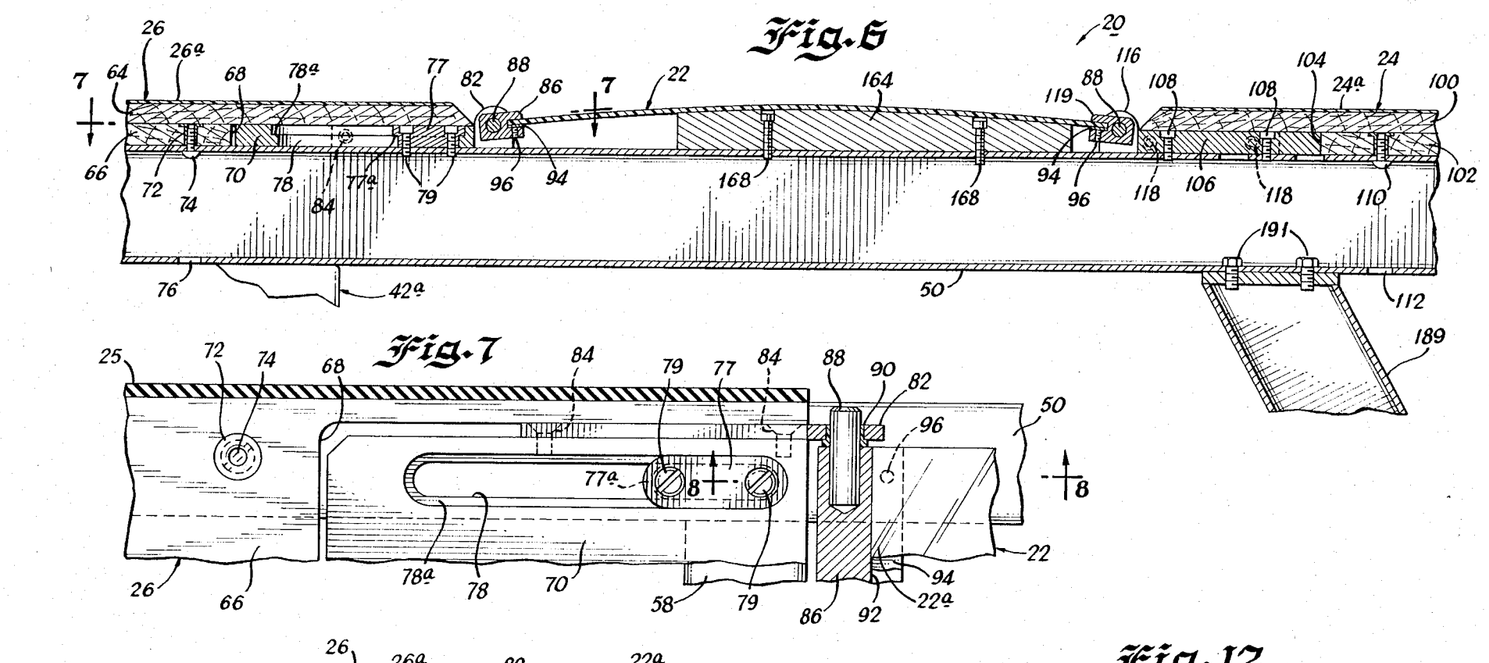
FIG. 6 is a cross sectional view taken along the line 6—6 of FIG. 3.
FIG. 7 is a plan sectional view taken along the lines 7—7 of FIG. 6 and shown on a somewhat larger scale.

In accordance with a further aspect of the invention, a pair of side support members 164 and 166 are provided under each edge of the transparent arch 22, the members 164, 166 being secured to the frame members 50, 52 by means of the screws 168 (FIG. 6). The members 164, 166 provide support for the transparent arch 22 when it is lowered to a minimum height position in which the top surface of the arch 22 is of the same height as the top surfaces of the head board 24 and hip board 26 and prevent the transparent arch 22 from collapsing under the weight of the patient when it is in the minimum height position shown in FIGS. 4 and 6. As is evident from these figures, the upper surface of the supports 164 and 166 is curved to match the slight upward arch of the transparent member 22 when in the minimum height position and prevents the arch 22 from buckling inwardly to a position in which the arch might be bowed downwardly rather than upwardly when the actuator 120 is energized to move the slide 70 to the right.

Since the actuator 120 is capable of exerting a substantial force, in the order of 500 pounds, against the slide 70, it is possible that this actuator could be moved to a point where it would damage the controlled portions of the table 20. In accordance with a further aspect of the present invention limit switches are provided to limit the travel of the translating member 128 of the actuator 120 even though the doctor continues to hold the control switch 160 in either the high or low position. More particularly, a pair of limit switches 170 and 172 are mounted on a bracket 174 which is clamped to the housing 126 of the actuator 120 by means of the clamp 176. The bracket 174 is provided with an offset flange 178 which slideably supports a control rod 180. One end of the control rod 180 is secured to and moves with a flange 182 secured to the bottom side of the slide 70 by means of the screw 184. The control rod 180 carries a first adjustable control member 186 which is positioned between the bracket 182 and the limit switch 172 and a second control member 188 which is adjustably positioned on the rod 180 on the free end thereof. When the doctor holds the control knob 160 in the low position so that the motor 124 is energized and moves the actuator in the direction to move the slide 70 to the left, this motion continues only until the control member 186 engages the limit switch 172 whereupon the motor 124 is deenergized even though the doctor continues to hold the control knob 160 in the low position. The position of the control member 186 is adjusted so that it strikes the limit switch 172 just as the arch 22 is lowered into engagement with the supports 164 and 166. In a similar manner when the doctor holds the control knob in the high position, the motor 124 is energized to move the slide 70 to the right, as viewed in FIG. 4, until the control member 188 engages the limit switch 170, as shown in FIG. 5, in which position the arch 22 is at its maximum height position shown in this figure.

Figure 9:
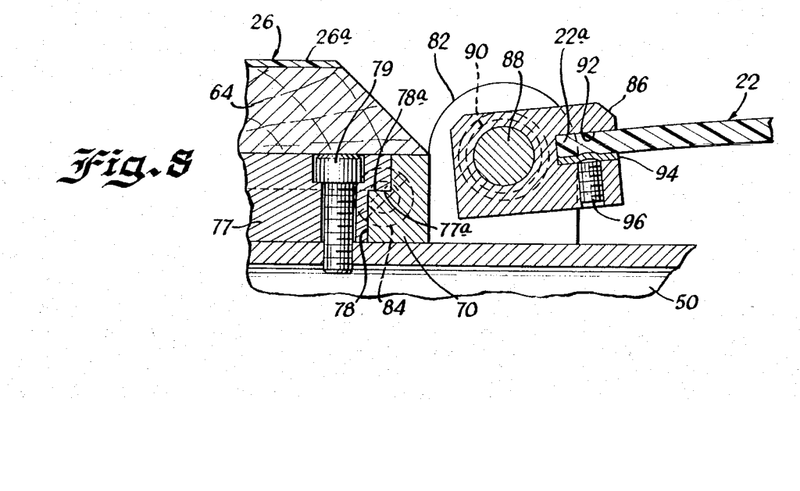
FIG. 9 is a sectional view taken along the lines 9—9 of FIG. 1.
Figures 10, 11:
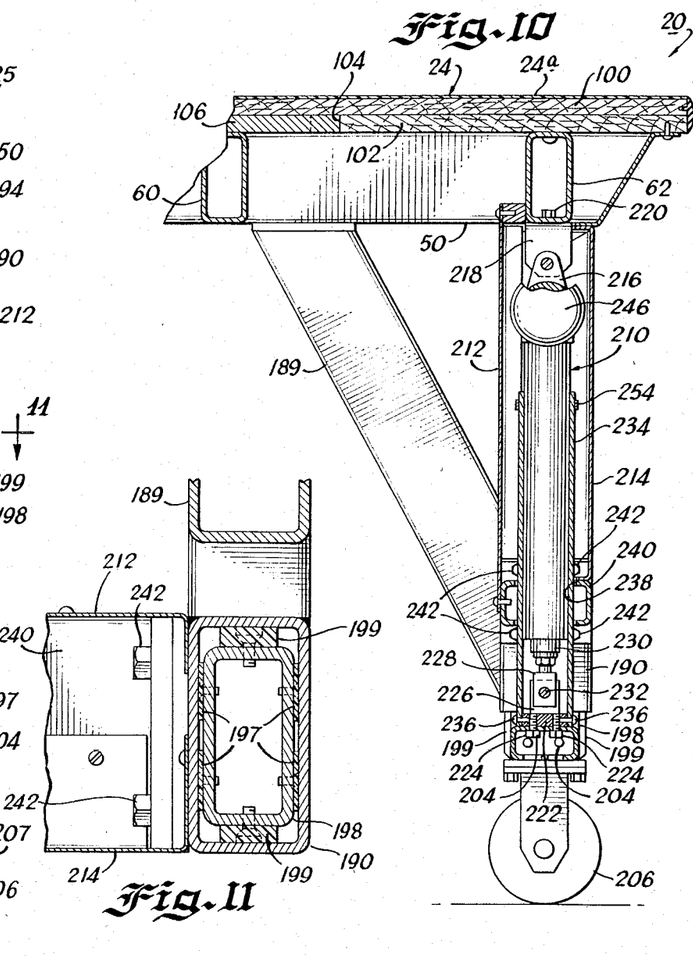
FIG. 10 is a cross sectional view taken along the lines 10—10 of FIG. 9.
FIG. 11 is a plane sectional view taken along the lines 11—11 of FIG. 9.

In accordance with a further aspect of the present invention the height of the table 20 may be adjusted automatically by control means readily and conveniently accessible to a doctor so that the patient may be moved to the most convenient height for that particular doctor to facilitate his insertion of a long needle into the patient's back. Adjustment of the height of the patient relative to the image intensifier cylinder 38 may also be desirable to obtain a properly focused picture on the screen of the X-ray equipment. More particularly, a motor driven linear actuator is positioned within an enclosed end section at each end of the table, these actuators being controllable by control means on the control panels 42, 42a. More particularly, and considering the right hand end of the table, as shown in FIGS. 9 and 10, a pair of tubular fixed legs 190 and 192 are secured to the side rails 50, 52 by means of the bolts 194 and 196, respectively. A pair of tubular leg extensions 198 and 200 are telescopically positioned within the fixed legs 190, 192 and are connected together at the bottom ends thereof by means of the tubular cross member 202 connected thereto by means of the bolts 204. In order to provide a firm but slideable joint between the legs 190, 192 and the leg extensions 198, 200, guide strips 197 and 199, which are preferably of ultra high molecular weight polyethylene, are secured to the long and short sides, respectively, of the leg extensions 198, 200, as best illustrated in FIG. 11. A pair of wheels 206, provided with locking means 207, are mounted on the ends of the leg extensions 198 and 200. Each of the fixed legs 190, 192 includes a tubular brace member 189 (FIG. 10) which is welded to the fixed leg and is secured to the side bar 50, or 52 be means of the bolts 191 to provide a rigidly braced support for the table 20 while permitting free access to the space beneath the transparent arch 22. A handle 21 (FIG. 1) is provided at the left hand end of the table 20 beneath the hip board 26 so that the table 20 may be easily moved to a desired position.

In order to raise and lower each end of the table separately, a motor driven lead screw actuator indicated generally at 210 is positioned between the cross member 62, at the right hand end of the table 20, and the cross member 202 connected to the leg extensions 198 and 200. A pneumatic or hydraulic actuator may also be used in place of the motor driven actuator 210, as discussed heretofore in connection with the actuator 120. Furthermore, as best illustrated in FIG. 10, the actuator 210 is positioned within the outer surfaces of the fixed legs 190, 192 and inner and outer covers 212 and 214 are provided so that the means for raising and lowering each end of the table is totally enclosed. The pivot mount 216 of the actuator 210 is pivotally connected to the brackets 218 which are secured to the underside of the cross member 62 by means of the bolts 220. A lower clevis block 222, which is secured to the upper surface of the cross member 202 by means of the bolts 224 is provided with a pair of upstanding flanges 226 which receive the clevis 228 attached to the end of the translating output member 230 of the actuator 210 by means of the pin 232. A tubular shield member 234 is secured at its bottom end to the clevis block 222 by means of the bolts 236 and extends upwardly through a clearance opening 238 in a tubular cross member 240 which is connected to the fixed legs 190, 192 by means of the bolts 242.

Considering now the manner in which the motor 246 of the lead screw actuator 210 may be energized and controlled to raise or lower the head end of the table 20, each of the control panels 42, 42a includes a first control knob 248 and a second control knob 250. The control knob 248 is spring biased to a right hand "NORMAL" position in which the actuators at both ends of the table are simultaneously moved in the same direction to either raise or lower the table in dependence upon the position of the control knob 250. In accordance with a further aspect of the invention the control knob 248 may be moved to a left hand "TREN." position, against such spring bias, so that the table is rapidly moved to approximate the so-called Trendelenburg position in which the patient's feet are elevated with respect to his head. The need for such position may arise in connection with certain medical treatments which may involve the use of an anesthetic, during which, the patient goes into shock and it is necessary to bring the blood quickly to the patient's head. More particularly, when the control knob 248 is held in this left hand position the actuator 210 is controlled to lower the head end of the table while the actuator in the foot end of the table is controlled simultaneously to raise the foot end of the table. During such action it is assumed that the control knob 250 is in its neutral position. As a result, with the arrangement of the present invention the feet of the patient may be very quickly raised relative to his head.

Assuming that the control knob 248 is in the right hand "NORMAL" position in which both ends of the table are simultaneously controlled in the same direction, when the doctor moves the control knob 250 to the left from its spring biased neutral central position, i.e., to the position identified as "RAISE" in FIG. 12, the motor 246 is energized so as to extend the output member 230 of the actuator 210 so that the right hand end of the table together with the fixed legs 190 and 192 is elevated relative to the leg extensions 198, 200 and the cross member 202. Such action continues as long as the doctor holds the control knob 250 in the left hand "RAISE" position. When the table has been raised to its maximum height the cross bar 240 engages a limit switch 252 which is secured to the upper end of the sleeve 234 by means of the clamp 254 so that the motor 246 is deenergized. Preferably, the speed of the motor 246 and gear reduction within the actuator 210 are arranged so that the table 20 may be raised to its maximum height in approximately 15 seconds. This rate of elevation of the table permits the doctor to make precision height adjustments as may be needed in chemonucleoloysis treatments, other treatments involving an X-ray image intensifier unit, or other patient treatments in general. Furthermore, the feet of the patient may be raised relative to his head at twice this speed in accordance with the present invention by releasing the knob 250 and moving the knob 248 to the left hand "TREN." position, as described heretofore.

When the control knob 250 is urged to the right from its neutral position i.e., to the "LOWER" position, the motor 246 is energized to retract the member 230 of the actuator 210 and lower the table 20. When the table 20 reaches a minimum height position i.e., when the member 230 of the actuator 210 is fully retracted an internal clutch in the actuator 210 disconnects the output member 230 from the motor 246 and the table remains in this minimum height position even though the control knob 250 is still held in the "LOWER" position by the doctor.

Figures 13, 14, 15, 16:
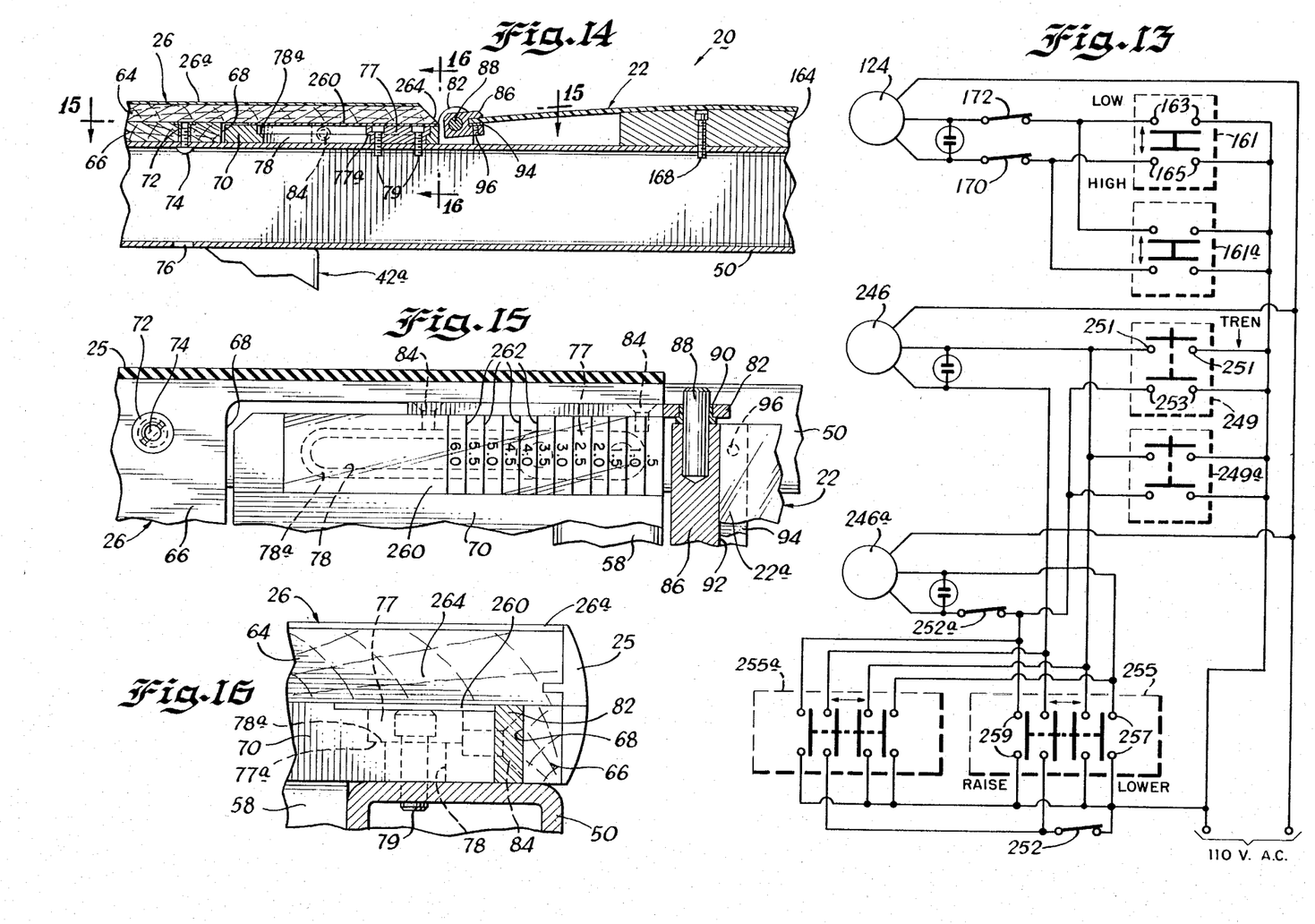
FIG. 13 is a circuit diagram showing the manner in which the table of FIG. 1 is controlled in accordance with the present invention.
FIG. 14 is a view similar to FIG. 6, showing an alternative embodiment of the invention wherein indicating means are provided for the arch member.
FIG. 15 is a view similar to FIG. 7 and also showing said alternative embodiment.
FIG. 16 is a sectional view taken along the lines 16—16 of FIG. 14.

As discussed generally heretofore, the left hand end of the table 20 is constructed identically to the above described right hand end portion and a lead screw actuator identical to the actuator 210 is provided within the enclosed left hand leg section. More particularly, this actuator is provided with a motor 246a connected as shown in FIG. 13. Referring to this figure, the control knob 248 controls a switch 249 the contacts 251 and 253 of which are open when the control knob 248 is in the right hand position i.e., the "NORMAL" position. The control knob 250 controls a switch 255 having the normally open contacts 257 and 259. When the control knob 250 is moved to the "LOWER" position the contacts 257 are closed so that both motors 246 and 246a are rotated in the correct direction to lower both ends of the table simultaneously. Conversely, when the control knob 250 is moved to the "RAISE" position the contacts 259 are closed so that both motors 246 and 246a are rotated in the opposite direction to raise the table 20. However, when the knob 248 is held in the left hand or "TREN." position the contacts 253 are closed so that the motor 246a associated with the linear actuator in the left hand leg section of the table 20 is energized to raise the foot end of the table while at the same time the contacts 251 are closed so that the motor 246 is simultaneously energized to lower the head end of the table. The control knob 160 controls a switch 161 having the normally open contacts 163 and 165. When the knob 160 is moved to the arch low position the contacts 163 are closed and the motor 124 is energized to retract the member 128 and lower the arch 22. When the control knob 160 is moved to the arch high position the contacts 165 are closed and the motor 124 is energized to extend the member 128 and raise the arch 22. It will be understood that the switches 161a, 249a and 255a are provided in the control box 42a on the opposite side of the table and perform similar functions, as will be readily apparent from FIG. 13. In this connection it should be noted that the raise limit switch 252 associated with the motor 246 at the head end of the table controls both of the motors 246 and 246a whereas the raise limit switch 252a controls only the motor 246a at the foot end of the table. The motors 246 and 246a are capacitor start motors and it has been found that the limit switch 252 must be placed outside the normally open switches 255, 255a to prevent continuous current drain through the capacitors of these motors.

If the position of the foot end of the table 20 has been elevated relative to the head portion thereof, the table 20 may be readily brought back to a horizontal position by moving the control knob 250 to the "LOWER" position which closes the contacts 257. When the head end of the table reaches the minimum height position before the foot end, the clutch associated with the actuator 210 slips while the motor 246a driving the foot actuator continues to lower that end of the table, which is still higher, until both ends of the table are at the same minimum height, at which position the clutches associated with both of the linear actuators come into effect and the table 20 is horizontal at minimum height. It is also possible to level the table 20 by moving the control knob 250 to the "RAISE" position so that the contacts 259 are closed. When the foot end of the table, which has been elevated, reaches maximum height its limit switch 252a deenegerzies the motor 246a while the motor 246 continues to raise the head end of the table. When the head end of the table is also at maximum height the limit switch 252 also opens and the table is horizontal.

In accordance with a further aspect of the invention, and as discussed generally heretofore, means are provided for indicating the position of the slide 70, said means being calibrated in terms of the height of the arch 22 above the head board 24 and hip board 26. More particularly, as shown in FIGS. 14, 15 and 16, a slot cover strip 260, preferably of mylar, is adhesively secured over each of the slots 78 in the slide member 70 at each side of the table 20. Suitable indicia 262 are provided along the length of the strip 260 which may be read relative to the fixed mitred edge 264 of the hip board 26 as the slide 70 is moved by the actuator 120. The indicia 262 are in terms of the height of the arch 22 relative to the top surfaces of the head board 24 and hip board 265 so that the doctor does not have to guess the height to which he has adjusted the arch 22. The cover strips 260 also serve the function of covering the slots 78 so that when the arch 22 is being lowered and the slide 70 is retracting beneath the edge of the hip board 26 it is not possible for a finger to be pinched within the slots 78.

While there have been described what are at present considered to be the preferred embodiments of the invention, it will be understood that various modifications may be made therein which are within the true spirit and scope of the invention.

What is claimed as new and is desired to be secured by Letters Patent of the United States is:

1. A patient treatment table, comprising a table frame, a hip board fixedly secured to said frame, a head board fixedly secured to said frame and spaced from said hip board, a transparent, flexible arch member positioned between said head board and said hip board and extending across the entire width of the space between said head board and said hip board, a rigid slide member extending across the table adjacent to and beneath the inner edge of said hip board and pivotally connected to one end of said arch member, means pivotally connecting said other end of said arch member to said frame adjacent said head board, and means for moving said slide member in a horizontal plane so that said one end of said arch member moves away from said fixed hip board and said arch member is bowed upwardly above the surface of said hip board and said head board, said arch member when in said bowed positon being sufficiently rigid to support by itself a substantial weight placed thereon.

2. A treatment table according to claim 1, which includes an arch support member pivotally mounted on said frame and extending across the table adjacent the edge of said head board, said arch support member having a slot extending along the length thereof, and means securing said other end of said arch member in said slot of said arch support member, said arch support member pivoting relative to said frame as said arch member is bowed upwardly to reduce stress in said other end of said arch member.

3. A treatment table according to claim 1, which includes an arch support member pivotally mounted on said slide member and having a slot extending along the length thereof, and means for securing said one end of said arch member in said slot of said arch support member, said arch support member pivoting relative to said slide member as said arch member is bowed upwardly to reduce stress in said one end of said arch member.

4. A treatment table according to claim 1, wherein said slide member has a slot in each end thereof and extending along the length of said table, and a pair of fixed guide keys positioned in said slots to guide horizontal movement of said slide member as said arch member is bowed upwardly.

5. A treatment table according to claim 1, which includes driving means mounted on said frame and connected to said slide member for moving said slide member toward said head board and thereby bowing said arch member upwardly above the surface of said head board and said hip board said hip board remaining fixed in position during said movement of said slide member.

6. A treatment table according to claim 5, wherein said driving means comprises a lead screw actuator having an output member connected to said slide member, and a power source for rotating the screw portion of said actuator.

7. A treatment table according to claim 6, which includes control means for said power source carried by said frame adjacent said arch member for selectively energizing said power source so that said slide member may be moved in either direction to control the extent to which said arch member is bowed.

8. A treatment table according to claim 7, which includes limit switch means for disabling said electric motor, and means movable with said slide member for actuating said limit switch means when said arch member has been moved to a predetermined minimum height position.

9. A treatment table according to claim 1, wherein said arch member comprises a sheet of flexible material of uniform thickness throughout its width and having sufficient strength that it can support the weight of a patient without requiring edge reinforcement.

10. A treatment table according to claim 9, wherein said sheet material has a thickness of approximately 3/16 of an inch.

11. A treatment table according to claim 9, wherein said arch member is made of a vinyl compound having a high resistance to fatigue under repeated flexing of said arch member.

12. A patient treatment table according to claim 11, which includes means for indicating the positon of said slide member relative to a fixed portion of the table, said indicating means providing an indication of the height of said flexible arch portion relative to said head and hip board portions.

* * * * *

UNITED STATES PATENT AND TRADEMARK OFFICE
CERTIFICATE OF CORRECTION

PATENT NO. : 4,520,800
DATED : June 4, 1985
INVENTOR(S) : Frank P. Kowalski

It is certified that error appears in the above-identified patent and that said Letters Patent are hereby corrected as shown below:

Column 14, line 22, "11" should read --1--.

Signed and Sealed this

Thirty-first Day of December 1985

[SEAL]

Attest:

DONALD J. QUIGG

Attesting Officer

Commissioner of Patents and Trademarks